(12) United States Patent
Jeon (10) Patent No.: US 9,089,697 B2
(45) Date of Patent: Jul. 28, 2015

(54) X-RAY NEEDLE MODULE FOR LOCAL RADIATION THERAPY

(75) Inventor: In Su Jeon, Gwangju (KR)

(73) Assignee: Industry Foundation of Chonnam National University, Gwangju (KR)

(*) Notice: Subject to any disclaimer, the term of this patent is extended or adjusted under 35 U.S.C. 154(b) by 101 days.

(21) Appl. No.: 13/813,329

(22) PCT Filed: May 9, 2012

(86) PCT No.: PCT/KR2012/003624
§ 371 (c)(1),
(2), (4) Date: Jan. 30, 2013

(87) PCT Pub. No.: WO2012/173341
PCT Pub. Date: Dec. 20, 2012

(65) Prior Publication Data
US 2013/0121474 A1 May 16, 2013

(30) Foreign Application Priority Data
Jun. 14, 2011 (KR) .................. 10-2011-0057240

(51) Int. Cl.
*A61N 5/10* (2006.01)
*H01J 35/16* (2006.01)
*H05G 1/02* (2006.01)
*G02B 5/08* (2006.01)
*H01J 35/18* (2006.01)
(Continued)

(52) U.S. Cl.
CPC ............ *A61N 5/1077* (2013.01); *A61N 5/1027* (2013.01); *A61N 5/1042* (2013.01); *G02B 5/0875* (2013.01); *H01J 35/165* (2013.01); *A61B 6/06* (2013.01); *A61B 6/08* (2013.01); *A61N 2005/1022* (2013.01); *G02B 5/0816* (2013.01); *H01J 35/16* (2013.01); *H01J 35/18* (2013.01)

(58) Field of Classification Search
USPC ............ 378/64, 65, 140, 145, 147, 149, 197, 378/198, 204, 210; 359/883
See application file for complete search history.

(56) References Cited

U.S. PATENT DOCUMENTS 4,675,889 A * 6/1987 Wood et al. .................. 378/84
4,958,363 A * 9/1990 Nelson et al. ................. 378/85
(Continued)

FOREIGN PATENT DOCUMENTS

| JP | 07-39592 A | 2/1995 |
| JP | 09-178676 A | 7/1997 |
| KR | 10-0997419 B1 | 11/2010 |

OTHER PUBLICATIONS

International Search Report of PCT/KR2012/003624 dated Dec. 3, 2012.

*Primary Examiner* — Anastasia Midkiff
(74) *Attorney, Agent, or Firm* — Lucas & Mercanti, LLP (57) ABSTRACT

The present invention provides an X-ray needle module for local radiation therapy containing: an X-ray generating part supplied with external electric power; and an X-ray needle forming part which collects the X-rays generated by the X-ray generating part and extracts the collected X-rays into high-intensity short-wavelength parallel X-rays so as to form an X-ray needle. The X-ray needle forming part includes a housing with an entrance hole at one surface through which the X-rays generated by the X-ray generating part enter and an exit hole at another surface through which the X-ray needle exits, the X-ray needle, provided in the housing, which collects the X-rays generated by the X-ray generating part and forms the X-ray needle of the high-intensity short-wavelength parallel X-rays and a position controller, provided at a leading end of the X-ray mirror.

5 Claims, 8 Drawing Sheets (51) Int. Cl.
   *A61B 6/08* (2006.01)
   *A61B 6/06* (2006.01)

(56) References Cited

U.S. PATENT DOCUMENTS

| | | | |
|---|---|---|---|
| 6,014,423 A * | 1/2000 | Gutman et al. | 378/85 |
| 6,359,963 B1 * | 3/2002 | Cash | 378/65 |
| 6,421,417 B1 * | 7/2002 | Jiang et al. | 378/84 |
| 7,076,026 B2 * | 7/2006 | Verman et al. | 378/85 |
| 7,430,277 B2 * | 9/2008 | Hoghoj et al. | 378/84 |
| 8,092,370 B2 * | 1/2012 | Roberts et al. | 600/38 |
| 2006/0133575 A1 * | 6/2006 | Gutman et al. | 378/119 |
| 2009/0141342 A1 * | 6/2009 | Kessels et al. | 359/359 |

* cited by examiner

Fig. 1

CONCEPTUAL VIEW OF GENERAL RADIATION THERAPY

CONCEPTUAL VIEW OF CYBERKNIFE THERAPY

X-RAY NEEDLE MODULE FOR LOCAL RADIATION THERAPY

CROSS-REFERENCE TO RELATED APPLICATIONS

This application is a 371 of PCT/KR2012/003624 filed on May 9, 2012, which claims the benefit of Korean Patent Application No. 10-2011-0057240 filed on Jun. 14, 2011, the contents of each of which are incorporated herein by reference.

TECHNICAL FIELD

The present invention relates to an X-ray needle module for local radiation therapy, and more particularly to an X-ray needle module for local radiation therapy which is needed to conduct a novel radiation therapy, which generates an X-ray needle composed of high-intensity short-wavelength parallel X-rays by controlling X-rays which are likely to radially spread, and then irradiates cancer tissue with the X-ray needle so as to minimize damage to healthy tissues other than the cancer tissue.

BACKGROUND ART

Radiation therapy is a disease treatment using radiation such as X-rays, gamma rays, and proton beams. This retards or stops the growth of cancer tissues or various tissues of malignant diseases, and even kills such tissues.

In Korea, the number of new domestic cancer patients was 161,920 in 2007, and the occurrence frequency of cancers descends in order of stomach cancer, lung cancer, liver cancer, and cervical cancer. X-rays most dominantly play a role in treating cancers among diverse radiation treatments.

Generally, an X-ray treatment is a local/regional control therapy to treat a cancer in a region where it is difficult to undergo an operation for such reasons that the size of a tumor is very large and the depth of invasion is deep, or to treat a cancer which remains after an operation. Statistically, 60% of cancer patients undergo X-ray therapy.

Figure 1:
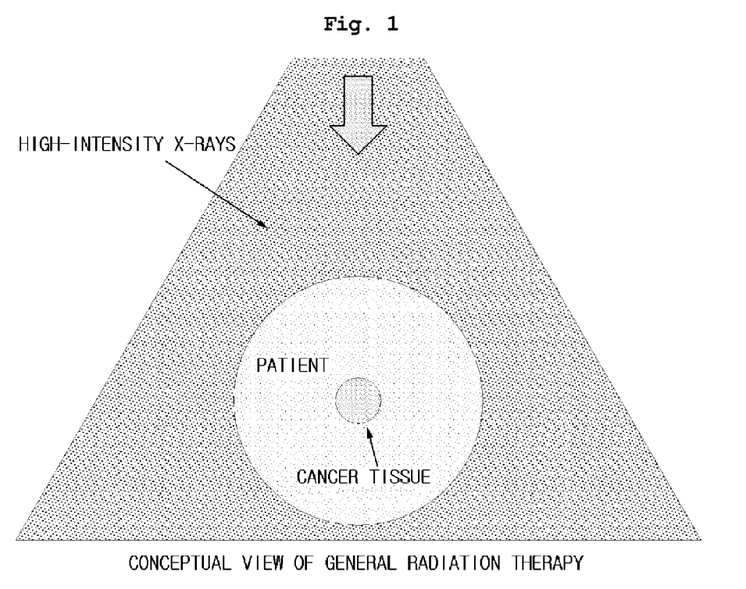
FIGS. 1 to 3 are conceptual diagrams illustrating X-ray therapies according to related arts.

In a conventional X-ray treatment, regional exposure of only the cancer tissue to X-rays is difficult to attain due to the characteristics of the X-rays which are emitted in a radial direction from an X-ray source, as illustrated in FIG. 1. That is, healthy cells and tissues in the vicinity of the cancer are also exposed to the X-rays. For this reason, a patient who undergoes the X-ray treatment suffers from side effects such as damage to healthy cells and tissues, hair loss, weakened immune system, and other complications.

In order to solve this problem, Intensity-Modulated Radiation Therapy (IMRT), Tomotherapy, Cyberknife therapy using a small linear accelerator, and the like have been developed and used.

Figure 2:
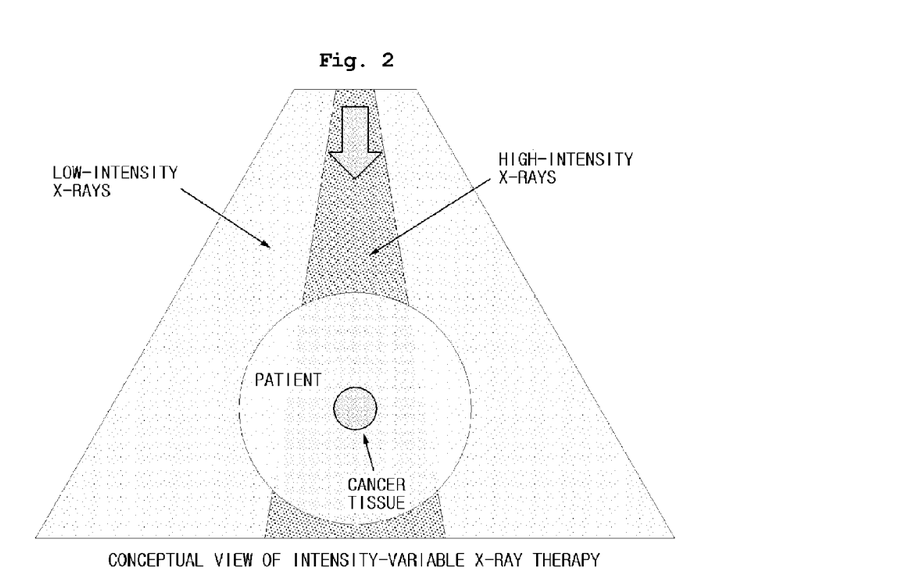

However, in the case of IMRT and Tomotherapy, it is unavoidable that a large area including cancer tissue is exposed to X-rays, as illustrated in FIG. 2.

Figure 3:
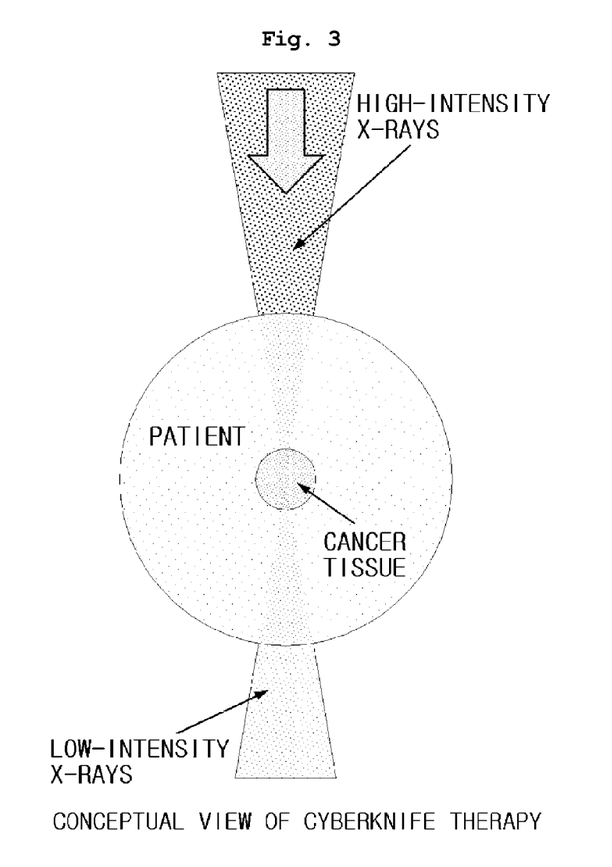

In the case of Cyberknife therapy, X-ray focusing is performed as illustrated in FIG. 3 so that highly-intensified narrow X-rays can be irradiated in various directions. Therefore, the Cyberknife therapy can be used for local therapy on the cancer tissue. However, the X-rays remain without being absorbed by the cancer cells or tissue after the focused X-rays are used to kill the cancer tissue, and scatter in all directions, negatively effecting human bodies. Therefore, the problem mentioned above still remains unsolved.

Accordingly, development of a novel radiation therapy which can minimize damage to healthy tissue other than patient's cancer tissue is still in demand.

DISCLOSURE

Technical Problem

Therefore, the present invention has been made keeping in mind the above problems occurring in the related art, and is intended to propose an X-ray needle module for local radiation therapy which enables a local/area-limited X-ray therapy applied only to cancer tissue by generating a needle of high-intensity short-wavelength parallel X-rays with use of an X-ray mirror which collects X-rays and extracts the high-intensity short-wavelength parallel X-rays, so as to minimize damage to healthy tissue other than cancer tissue.

Technical Solution

In order to achieve the object, according to one aspect, the present invention provides an X-ray needle module for local radiation therapy including: an X-ray generating part which is supplied with external electric power and generates X-rays; and an X-ray needle forming part which collects the X-rays generated by the X-ray generating part and extracts the collected X-rays into high-intensity short-wavelength parallel X-rays so as to form an X-ray needle, wherein the X-ray needle forming part includes a housing with an entrance hole at one surface through which the X-rays generated by the X-ray generating part enter and an exit hole at another surface through which the X-ray needle exits, an X-ray mirror, provided in the housing, which collects the X-rays generated by the X-ray generating part to form the X-ray needle of the high-intensity short-wavelength parallel X-rays, and a position controller, provided at a leading end of the X-ray mirror, which controls an installation angle of the X-ray mirror.

A connecting part may be further provided between the X-ray generating part and the X-ray needle forming part to connect the X-ray generating part and the X-ray needle forming part to each other.

A coupling part may be further provided at one side of the X-ray generating part to couple the X-ray needle module to a robot structure so that degrees of freedom in movement may be achieved.

The X-ray mirror may be manufactured by preparing a core using a geometric form designed in advance, applying and curing a polymer material (SU8) on an upper surface of the core, separating the cured polymer material, and obtaining a multi-layered thin-film X-ray mirror by forming a multi-layered thin-film laminate composed of two kinds of metal layers having different densities which are alternately laminated.

The core may be made from an aluminum plate coated with nickel or from glass or silicone, either of which is surface-machined to have surface roughness Ra of 1 to 3 nm.

The multi-layered thin-film laminate may be prepared by recomputing X-ray reflectivity with respect to the X-ray mirror, and then by determining a suitable thickness ratio tA/tB of the two kinds of metal layers A and B having the different densities. The polymer material may be a polymer such as SU8.

Advantageous Effects

According to the present invention, in the X-ray needle module for local radiation therapy, X-rays generated by the X-ray generating part may be collected by the X-ray mirror so as to form the high-intensity short-wavelength parallel X-rays. Then, the high-intensity short-wavelength parallel X-rays may serve as the X-ray needle and may be locally radiated to cancer tissue. In this way, it is possible to minimize damage to healthy tissues in the human body.

Further, since the X-ray needle with an invariable width is formed unlike in the X-ray focusing of the conventional Cyberknife therapies, the X-rays are absorbed by the cancer tissue after they are radiated to kill the cancer tissue, and this maximizes cancer treatment effects. In addition, the present invention has advantages of minimizing side effects which occur in a patent under treatment and promoting recovery of the patient under treatment.

Further, since the X-rays generated by the X-ray generating part may be extracted into the high-intensity short-wavelength parallel X-rays using the X-ray mirror, a simplified structure and a competitive price may be attained. Further, the X-ray needle module may be coupled to a robot structure so as to enable multiple degrees of freedom (DOF), thereby achieving greater precision and effectiveness in the treatment of cancer.

BEST MODE

Reference will now be made in greater detail to a preferred embodiment of the invention, and objects, features, and advantages of the present invention will become more apparent by referring to the preferred embodiment. An X-ray needle module for local radiation therapy according to the present invention will be described in greater detail with reference to the accompanying drawings. Wherever possible, the same reference numerals will be used throughout the drawings and the description to refer to the same or like parts.

Figure 4:
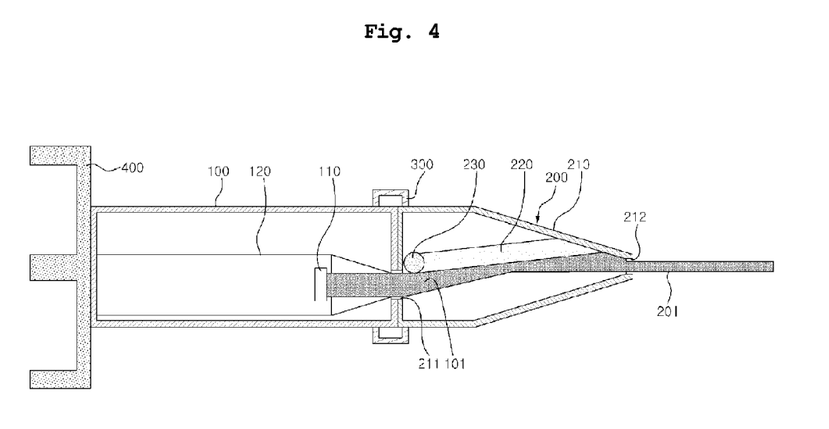
FIG. 4 is a diagram illustrating the schematic structure of an X-ray needle module for local radiation therapy according to the present invention.
Figure 5:
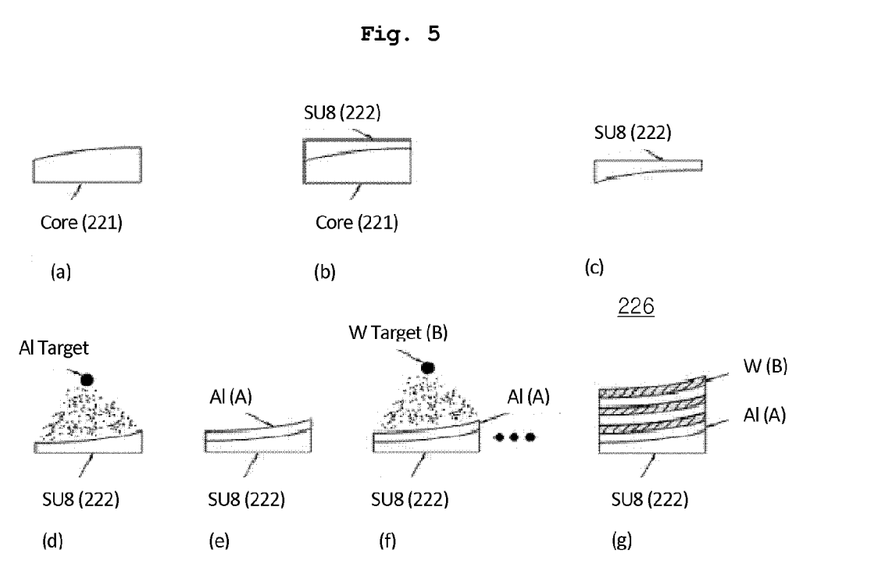
FIG. 5 is a diagram illustrating a manufacturing process of an X-ray mirror according to the present invention.
Figure 6:
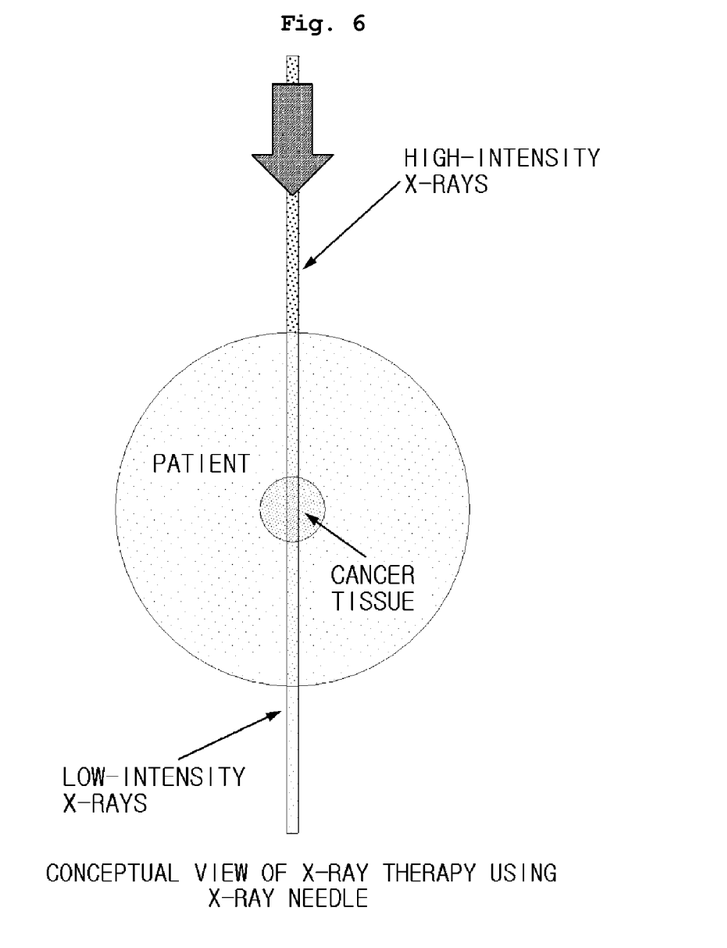
FIG. 6 is a diagram illustrating the concept of an X-ray therapy using the X-ray needle module for local radiation therapy according to the present invention.

FIG. 4 is a diagram illustrating the schematic structure of an X-ray needle module for local radiation therapy according to the present invention; FIG. 5 is a diagram illustrating a manufacturing process of an X-ray mirror according to the present invention; and FIG. 6 is a diagram illustrating the concept of X-ray therapy using the X-ray needle module for local radiation therapy according to the present invention.

As illustrated in FIG. 4, the X-ray needle module for local radiation therapy according to the present invention includes an X-ray generating part 100 which is supplied with external power and generates X-rays 101, and an X-ray needle forming part 200 which collects the X-rays 101 generated by the X-ray generating part 100 and abstracts the collected X-rays 101 into high-intensity short-wavelength parallel X-rays 201 to form an X-ray needle.

Here, the X-ray generating part 100 includes a source 110 which is supplied with external power and generates the X-rays. The source 110 is preferably installed in a manner such that the source 110 is situated close to and coupled to X-ray optical parts provided in a housing. The electric power is supplied to the source 110 from an electric generator (not shown). In addition, the X-ray generating part 100 may be an X-ray generating device that generates X-rays by shooting an energy beam to a target, or may be other types of X-ray generating means.

The X-ray needle forming part 200 is equipped with the X-ray mirror 220. The X-ray mirror 220 is installed in a housing with an entrance hole 211 through which the X-rays 101 generated by the X-ray generating part 100 enter and which is provided at one side, and an exit hole 212 which is provided at another side. The X-ray mirror 220 collects the X-rays which have entered through the entrance hole 211, forms the high-intensity short-wavelength parallel X-rays 201 which have the same width as the original X-rays, and causes the parallel X-rays 210 to proceed through the exit hole 212.

Here, the X-ray mirror 220 collects the X-rays emitted from the X-ray generating part 100 to extract the high-intensity short-wavelength parallel X-rays. The high-intensity short-wavelength parallel X-rays change in shape while passing through the exit hole 212 so as to become the X-ray needle 201, and the X-ray needle 201 travels forward.

To manufacture the X-ray mirror 220 used in the present invention, a thin-film X-ray mirror is prepared first. The thin-film X-ray mirror is manufactured as illustrated in FIG. 5. That is, s manufacturing process of the thin-film X-ray includes: (a) fabricating a core 221 in a geometrical form which has been designed in advance; (b) applying and curing a polymer material 222 such as SU8 on the upper surface of the core 221; (c) separating the cured polymer material; (d to f) forming a thin-film laminate composed of two kinds of metal layers A and B having different densities which are alternately laminated; and (g) obtaining a multi-layered thin-film X-ray mirror 26.

Before manufacturing the X-ray mirror 220, the geometric form of the X-ray mirror is designed in advance by taking the amplitude (2.289 Å) of a specific X-ray (for example, a Kα X-ray generated using a Cr-target X-ray source) into consideration. After finishing the designing, the core 221 having a surface roughness Ra of 1 to 3 nm is fabricated based on the geometric form.

In the course of designing the geometric form, a mirror equation for inducing the parallel X-rays from the X-rays which are in a constraint condition in which the X-rays reflected from the X-ray mirror 220 horizontally travel is determined in the following manner.

$$y^2 = ax + \frac{a^2}{4}$$

Figure 7:
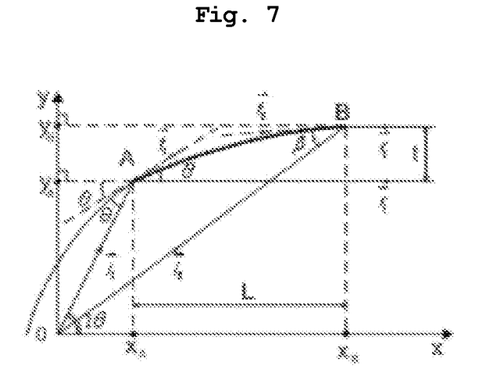
FIG. 7 is an Example of geometric design of a parallel X-ray forming mirror.

Here, x and y represents the curves of the mirror, and a constant "a" is determined depending on an initial point A of the curve of the mirror as in FIG. 7.

To increase an acceptable incidence angle θ of the X-ray mirror 220 illustrated in FIG. 6, the multi-layered thin-film X-ray mirror 226 in which two kinds of metal layers A and B having different densities are alternately laminated is fabricated. Reflectivity $X_j$ of the mirror is found through the following formula to determine the acceptable incidence angle θ.

$$\chi_j = \frac{r_j + \chi_{j+1} \cdot \exp(-i2\phi_j)}{1 + r_j \cdot \chi_{j+1} \cdot \exp(-i2\phi_j)}$$

$$\phi_j = \frac{2\pi}{\lambda} d_j n_j \sin\theta_j$$

(Herein, $d_j$ is the thickness of a j-th layer, $r_j$ is a Fresnell coefficient at a j-th interface, and i is a complex number.)

Figure 8:
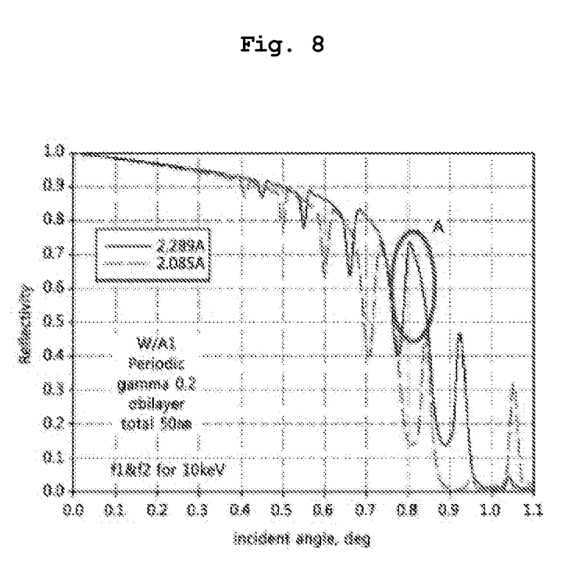
FIG. 8 is an X-ray reflectivity for incidence angle of X-ray.

It is necessary to compute the X-ray reflectivity to design the X-ray mirror 220. When fabricating the X-ray mirror, the X-ray reflectivity shown in FIG. 8 can be obtained by alternately laminating metal layers (for example, W and Al) having different densities after choosing a predetermined thickness ratio between the metal layers. FIG. 8 indicates the reflectivity of a W/Al multi-layered X-ray mirror which is designed to use a Cr-target X-ray source.

Specifically, as illustrated in FIG. 8, in the case of the X-ray mirror designed for use in the present invention, in order to form the parallel X-rays, an initial incidence angle θ of X-rays which are incident on one mirror is set to 0.86°, a final incidence angle β is set to 0.68°, and a difference between the initial incidence angle θ and the final incidence angle β is set to 0.18°. That is, the structure of the mirror is designed with the acceptable incidence angle of the X-ray mirror which is set to 0.86°, and two kinds of metal layers (for example, W/Al) having different densities are alternately laminated. With this structure, since the gap between the initial incidence angle θ and the final incidence angle β is narrow, reflection occurs only in an A region in FIG. 8. When considering a section in which the X-ray reflectivity in this region is 60% or more, a Kα X-ray is predominantly reflected and a Kβ X-ray is partly reflected. However, since the reflectivity of the Kβ X-ray is very low, the high-intensity parallel Kα X-rays having a substantially short wavelength can be formed by using only the designed X-ray mirror mentioned above.

The core 221 can be fabricated by using an ultra-precision surface machining machine, based on the geometric form of the parallel X-ray mirror 220 designed in the described manner. The core 221 is made from an aluminum plate coated with nickel, or is made of glass or silicone. The surface is machined to have a surface roughness Ra of 1 to 3 mm.

In preparing the multi-layered thin-film laminate, the reflectivity of X-rays with respect to the X-ray mirror 220 is recomputed, and then a suitable thickness ratio $t_A/t_B$ of two different kinds of metal layers A and B is preferably determined.

A position controller 230 is provided at a leading end of the X-ray mirror 220 to control an installation angle of the X-ray mirror 220.

A connecting part 300 to connect the X-ray generating part 100 and the X-ray needle forming part 200 is provided between the X-ray generating part 100 and the X-ray needle forming part 200. The connecting part 300 is preferably structured to enable connection and disconnection between the X-ray generating part 100 and the X-ray needle forming part 200.

In a portion of the X-ray generating part 100 connected to the X-ray needle forming part 200 by the connecting part 300, a coupling part 400 which allows the X-ray needle module to be coupled to a robot structure is provided to enable multiple degrees of freedom (DOF) in movement.

In the X-ray needle module for local radiation therapy configured in the manner described above, the X-rays 101 generated by the X-ray generating part 100 are collected by the X-ray mirror 220 after having passed through the entrance hole 211 of the X-ray needle forming part 200, the X-rays which are incident on the X-ray mirror 220 are converted into high-intensity parallel X-rays 201 having a substantially short wavelength, and the high-intensity parallel X-rays 201 are emitted through the exit hole 212 of the housing 210.

As illustrated in FIG. 6, the emitted high-intensity short-wavelength parallel X-rays 201 are changed into an X-ray needle with an invariable width, which is then radiated to local cancer tissue, thereby minimizing damage to tissue of the human body. In addition, the parallel X-ray needle with an invariable width is formed unlike in the conventional Cyberknife therapy. The X-ray needle is absorbed by the cancer tissue after killing the cancer tissue, and this maximizes the cancer treatment effect.

In addition, since the X-rays generated by the X-ray generating part 100 are extracted into the high-intensity short-wavelength parallel X-rays 210 using the X-ray mirror 220, a simplified structure and a competitive price may be achieved. Further, the X-ray needle module may be coupled to a robot structure so as to enable multiple degrees of freedom (DOF), achieving greater precision and effectiveness in the treatment of cancer.

Hereinabove, the preferred embodiments of the present invention have been described, but the present invention is not limited to a specific embodiment. That is, those skilled in the art will appreciate that various modifications, alterations, and changes are possible, without departing from the scope and spirit of the invention as disclosed in the accompanying claims, and all such appropriate modifications, alterations, and changes, and their equivalents, should be construed to fall within the scope of the present invention.

The invention claimed is:

1. An X-ray needle module for local radiation therapy, comprising:
    an X-ray generating part which is supplied with external electric power and generates X-rays; and
    an X-ray needle forming part which collects the X-rays generated by the X-ray generating part and extracts the collected X-rays into high-intensity short-wavelength parallel X-rays so as to form an X-ray needle,
    wherein
    the X-ray needle forming part includes a housing with an entrance hole at one surface through which the X-rays generated by the X-ray generating part enter and an exit hole at another surface through which the X-ray needle exits, an X-ray mirror which is provided in the housing and collects the X-rays generated by the X-ray generating part to form the X-ray needle of the high-intensity short-wavelength parallel X-rays, and a position controller which is provided at a leading end of the X-ray mirror and controls an installation angle of the X-ray mirror;
    the X-ray mirror is manufactured by preparing a core using a geometric form designed in advance, applying and curing a polymer material on an upper surface of the core, separating the cured polymer material, and obtaining a multi-layered thin-film X-ray mirror by forming a multi-layered thin-film laminate composed of two kinds of metal layers having different densities which are alternately laminated; and
    the X-ray needle module for local radiation therapy, wherein the core is made from an aluminum plate coated with nickel or from glass or silicone, either of which is surface-machined to have surface roughness Ra of 1 to 3 nm.

2. The X-ray needle module for local radiation therapy according to claim 1, further comprising:

a connecting part, provided between the X-ray generating part and the X-ray needle forming part, which connects the X-ray generating part and the X-ray needle forming part to each other.

3. The X-ray needle module for local radiation therapy according to claim 1, further comprising:
a coupling part, provided at one side of the X-ray generating part, which couples the X-ray needle module to a robot structure so as to enable degrees of freedom in movement.

4. The X-ray needle module for local radiation therapy according to claim 1, wherein the multi-layered thin-film laminate is prepared by recomputing X-ray reflectivity with respect to the X-ray mirror, and then by determining a suitable thickness ratio tA/tB of the two kinds of metal layers A and B having the different densities.

5. The X-ray needle module for local radiation therapy according to claim 1, wherein the polymer material is a polymer SU8.

* * * * *